United States Patent [19]

Callender, Jr.

[11] 3,996,931

[45] Dec. 14, 1976

[54] FRACTURED BONE SETTING FASTENER ASSEMBLY

[76] Inventor: George R. Callender, Jr., 4701 MacCorkle Ave., SE., Charleston, W. Va. 25314

[22] Filed: July 3, 1975

[21] Appl. No.: 593,101

[52] U.S. Cl. .................. 128/92 BA; 128/92 BB
[51] Int. Cl.² .................. A61F 5/04; A61B 17/18
[58] Field of Search .......... 128/92 R, 92 B, 92 BA, 128/92 BB, 92 BC, 92 D

[56] References Cited

UNITED STATES PATENTS 3,374,786   3/1968   Callender, Jr. ............ 128/92 BB Primary Examiner—Ronald L. Frinks
Attorney, Agent, or Firm—Clarence A. O'Brien; Harvey B. Jacobson

[57] ABSTRACT

A nailing apparatus for fractured femoral bones consisting of a sleeve member and a femoral fastening member, the latter having parallel slots opening through one end of the fastening member and being of different lengths. The sleeve is telescopingly engageable over the slotted end of the fastening member and is equipped with an inwardly projecting key for keying into one of the slots. The shorter slot limits movement of the key along the fastening member and the longer slot allows the sleeve member to be drawn onto the slotted end of the fastening member as far as desired. The end of the fastening member remote from the slots is equipped with anchoring means for anchoring to a femoral head and the sleeve member is equipped with a trochanteric plate for securement to both adjacent cortex portions by fastening means secured through the plate. The trochanteric plate may be disposed at any desired angle relative to the longitudinal axis of the sleeve member.

1 Claim, 5 Drawing Figures

FRACTURED BONE SETTING FASTENER ASSEMBLY

BACKGROUND OF THE INVENTION

Surgical fastener assemblies for holding fractured bone segments in place and in particular a femur have heretofore been devised employing various adjustment features. In general, such fastener devices have employed a guide sleeve embedded in one bone segment such as the upper segment of a femur in order to non-rotatably receive and adjustably hold one end of an axially elongated shaft or nail which extends through both fractured bone segments, with the end of the shaft opposite the guide sleeve being provided with structure for securing the shaft to the bone segment. Because of absorption occurring during the bone healing process, it has been necessary to accommodate a certain amount of telescoping movement between the shaft and the guide sleeve, under certain circumstances. On the other hand, it is sometimes desirable in the setting of fractured bone segments that the shaft be axially fixed relative to the guide sleeve requiring, therefore, another type of fastener assembly.

Various forms of surgical bone fastener assemblies are disclosed in U.S. Pat. Nos. 662,748; 1,033,187; 2,612,159; 2,621,653; 2,628,614; 2,672,861; 2,682,265; 2,702,543; 2,801,631; 2,834,342; 3,029,811 and 3,107,666.

SUMMARY OF THE INVENTION

The fastener assembly of the instant invention comprises an improvement over the fastener assembly disclosed in my prior U.S. Pat. No. 3,374,786.

The slotted nail of my previously patented fastener assembly included a short and a long slot with the short slot opening endwise outwardly of the adjacent nail end and a connecting slot extending peripherally about the nail and connecting the inner end portion of the short slot with the outer end portion of the long slot.

The nail of the fastener assembly of the instant invention also utilizes a short and long slot, but in a first form of nail disclosed the long slot open endwise outwardly of the nail and peripherally extending communicating slot communicates the outer end portions of the long slot with the outer end of the short slot. In a second disclosed form of nail the short slot and long slot each open endwise outwardly of the corresponding nail end.

The main object of this invention is to provide a bone fixation nail equipped with both a short slot and a long slot, but with at least the long slot opening endwise through the adjacent end of the nail.

Another object of this invention, in accordance with the immediately preceding object, is to provide a nail including a peripherally extending communicating or entrance slot extending between the outer end portion of the long slot and opening into the outer end of the short slot of the associated nail.

Yet another object of this invention is to provide a second form of nail wherein corresponding ends of both the short slot and the long slot of the nail open endwise outwardly through the adjacent end of the nail.

A final object of this invention to be specifically enumerated herein is to provide a bone fixation apparatus in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
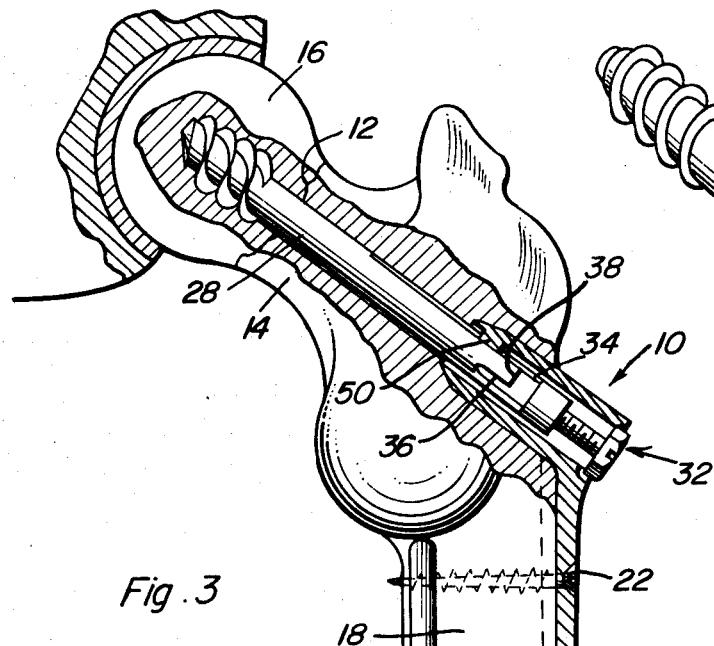
FIG. 1 is a side elevational view of a fractured hip bone set by use of a first form of fastener device of the instant invention with parts being broken away and shown in vertical section.
Figure 2:
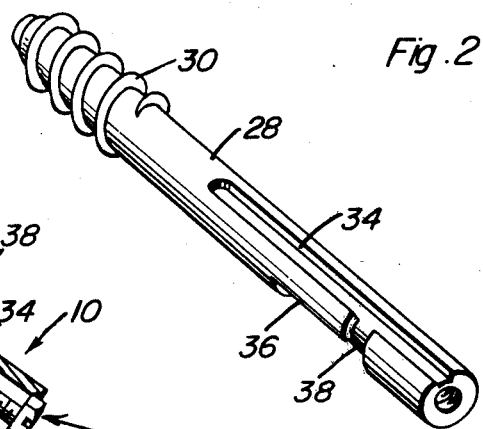
FIG. 2 is a perspective view of the nail portion of the fastener device.

Referring now more specifically to the drawings, the fastener assembly of the instant invention is generally referred to by the reference numeral 10 and is installed in a typical location in order to set a fracture occurring along the fracture line 12 through a femoral neck 14 between the femoral head 16 and the upper segment 18 of a femur. The fastener assembly 10 includes a guide portion generally referred to by the reference numeral 20 adapted to be fixedly secured to the upper segment of the femur by means of fasteners 22 extending through a trochanteric plate 24 to which a sleeve member 26 of the guide portion 20 is secured at a predetermined angle.

The bone segment 18 is bored to receive the sleeve member 26 and to receive an axially elongated shaft member 28 inserted through the sleeve member 26 and extending through the femoral neck 14 into the head 16. The end portion of the shaft member 28 remote from the sleeve member 26 is embedded within the bone segment or femoral head 16 by means of a surgical screw portion 30. The opposite end of the shaft member 28 is retained within the sleeve member 26 by means of an adjustable limit screw assembly referred to in general by the reference numeral 32 and which is illustrated and described in full detail in my above mentioned prior U.S. Pat. No. 3,374,786.

The elongated shaft member or nail 28 has two parallel longitudinal keyway grooves 34 and 36 formed therein. The groove 34 is longer than the groove 36 and opens endwise outwardly through the end of the nail 28 remote from the screw portion 30. The end of the shorter groove 36 remote from the screw portion 30 is closed, but is communicated with the corresponding end of the long groove 34 by peripherally extending connecting slot 38.

Figure 3:
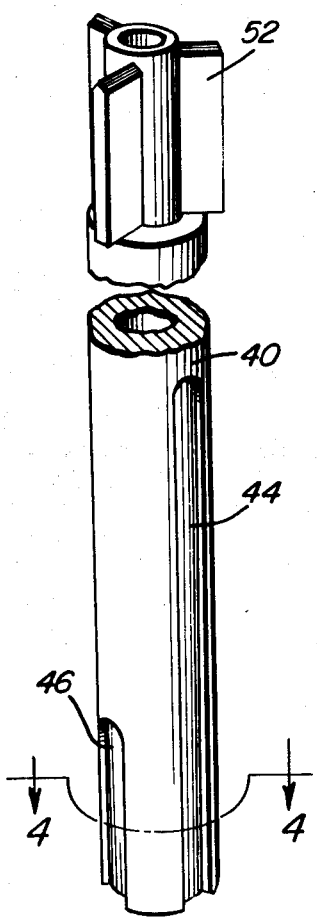
FIG. 3 is an enlarged perspective view of a second form of nail portion which may be used in the fastener assembly and having an intermediate portion thereof broken away.
Figure 4:
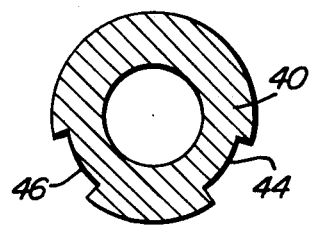
FIG. 4 is an enlarged horizontal sectional view taken substantially upon the plane indicated by the section line 4—4 of FIG. 3.
Figure 5:
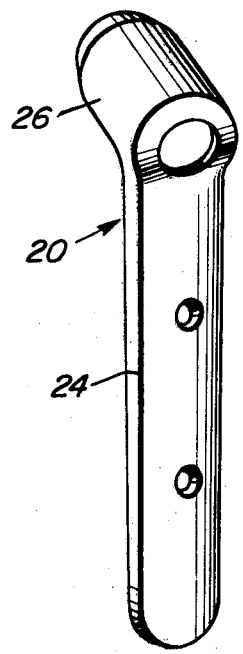
FIG. 5 is a perspective view of the sleeve and trochanteric plate assembly portion of the fastener assembly.

In the second form of shaft member or nail 40 illustrated in FIGS. 3 and 4 of the drawings long and short grooves 44 and 46 extend longitudinally of the nail 40 and each of the grooves 44 and 46 opens through the end of the nail 40 remote from the screw portion 48 corresponding to the screw portion 30 and the nail 40 does not include connecting slots corresponding to the slots. 38.

In operation, when a fixed length fastener is desired, the key 50 carried by the sleeve member 26 is keyed into the short slot 38 by introduction of the key 50 into the long groove 34, then rotation of the sleeve 26 relative to the nail 28 is effected to pass the key through the connecting slot 38 and into the short groove 36 whereupon the key 50 may be seated in the inner end of the groove 36, at which point the plate 24 contacts the bone segment 18 and may be secured thereto by means of the fastener 22. On the other hand, if an axially fixed fastener assembly is not desired, the key is inserted into one end of the slot 34 and the plate 24 is secured to the bone segment 18 by the fasteners 22. Thereafter, the screw assembly 32 may be adjusted in order to provide the desired axial compression along the fracture line 12.

With attention now invited more specifically to FIGS. 3 and 4 of the drawings, when the nail 40 is utilized in lieu of the nail 28 the key 50 may be readily introduced directly into either the long slot 44 or the short slot 46 without the necessity of effecting relative angular displacement of the nail 40 and the guide portion 20 in order to seat the key 50 in the inner end of the short slot 46.

Otherwise, the operation of the nail 40 in the method of its attachment and coaction with the guide portion 20 is substantially identical. Of course, it will be noted from the upper portion of FIG. 3 that the nail 40 is equipped with flange cutter elements 52, the equivalents of which flange cutter elements 52 are also fully described in my above-mentioned prior U.S. Pat. No. 3,374,786. Further, the long slot 44 is disposed in a radial plane of the nail 40 bisecting the included angle between radial planes in which adjacent elements 52 are disposed.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A surgical device for the fixation of fractured bones comprising, guide means adapted to be fixedly secured to one bone segment of a fractured bone, said guide means having a sleeve member adapted to extend into said bone segment, an axially elongated shaft member slidably received in and projecting from said sleeve member, said shaft member having a bone anchoring end portion remote from the sleeve member adapted to be embedded in the other bone segment of said fractured bone, limit means mounted on an end portion of the shaft member opposite said anchoring end portion for engagement with the guide means to limit axial extension of the shaft member in one direction from the sleeve member, relatively positionable key means on the sleeve and shaft members for alternatively accommodating telescoping movement between the members and axially locking the members against relative axial movement in both directions, said key means including a projection on said sleeve member and a single pair of parallel relatively long and short grooves formed in and extending longitudinally of the shaft member and in which said projection may be selectively engaged for sliding longitudinally therealong, the end of said long groove remote from said bone anchoring end portion opening endwise outwardly of the corresponding end of said shaft member and the corresponding end of said short groove being closed and spaced slightly from the corresponding end of said shaft member, said grooves including closed ends adjacent said anchoring end portion, the last-mentioned closed end of said long groove being closer to said anchoring end portion than the closed end of the short groove, and access means including a connecting slot formed in said shaft and extending thereabout with an end thereof opening into the closed end of said short groove remote from said anchoring end portion and the other end opening into said long groove at a point spaced from the end of said shaft member remote from said anchoring end portion.

* * * * *